United States Patent
Ye et al.

(10) Patent No.: US 10,424,396 B2
(45) Date of Patent: Sep. 24, 2019

(54) COMPUTATION PIPELINE OF LOCATION-DEPENDENT VARIANT CALLS

(71) Applicant: Sentieon Inc., Mountain View, CA (US)

(72) Inventors: Jun Ye, Palo Alto, CA (US); Wei Zhou, Saratoga, CA (US); Luoqi Chen, Saratoga, CA (US); Hanying Feng, San Jose, CA (US); Hong Chen, San Jose, CA (US); Xiaofeng Liu, Campbell, CA (US)

(*) Notice: Subject to any disclaimer, the term of this patent is extended or adjusted under 35 U.S.C. 154(b) by 643 days.

(21) Appl. No.: 15/080,538

(22) Filed: Mar. 24, 2016

(65) Prior Publication Data

US 2016/0283655 A1    Sep. 29, 2016

Related U.S. Application Data

(60) Provisional application No. 62/139,148, filed on Mar. 27, 2015, provisional application No. 62/143,013, filed on Apr. 3, 2015.

(51) Int. Cl.
| | |
|---|---|
| *G16B 30/00* | (2019.01) |
| *G16B 35/00* | (2019.01) |
| *G16C 20/60* | (2019.01) |
| *G16B 30/10* | (2019.01) |
| *G16B 20/00* | (2019.01) |

(52) U.S. Cl.
CPC ............ *G16B 30/00* (2019.02); *G16B 20/00* (2019.02); *G16B 30/10* (2019.02); *G16B 35/00* (2019.02); *G16C 20/60* (2019.02)

(58) Field of Classification Search
None
See application file for complete search history.

(56) References Cited

PUBLICATIONS

Mardis et al. A decade's perspective on DNA sequencing technology Nature vol. 470, pp. 198-203 (Year: 2011).*
Li et al. A survey of sequence alignment algorithms for next-generation sequencing Briefings in Bioinformatics vol. 11, pp. 473-483 (Year: 2010).*
Nielsen et al. Genotype and SNP calling from next-generation sequencing data Nature Reviews Genetics vol. 12, pp. 443-451 (Year: 2011).*
Cho et al. An ethnically relevant consensus Korean reference genome is a step towards personal reference genomes. Nature Communications vol. 7, article 13637 (Year: 2016).*
Zhao et al. Investigating single nucleotide polymorphism (SNP) density in the human genome and its implications for molecular evolution Gene vol. 312 pp. 207-213 (Year: 2003).*
Pabinger et al. A survey of tools for variant analysis of next-generation genome sequencing data Briefings in Bioinformatics vol. 15, pp. 256-278 (Year: 2013).*

* cited by examiner

*Primary Examiner* — John S Brusca
(74) *Attorney, Agent, or Firm* — Jun He Law Offices P.C.; James J. Zhu (57) ABSTRACT

The present disclosure provides a computer-implemented method for analyzing variants from a plurality of nucleic acid sequence reads using a computation pipeline, which comprises a module depending on a location-dependent parameter. The method comprises executing on a processor the steps of: receiving a plurality of nucleic acid sequence reads comprising at least a first nucleic acid sequence read and a second nucleic acid sequence read; mapping the first nucleic acid sequence read and the second nucleic acid sequence read to a first location and a second location in a genome, respectively; setting a first value and a second value for the location-dependent parameter on the basis of the first location and the second location in the genome, respectively; passing the first nucleic acid sequence read and the second nucleic acid sequence read through the module using the first value and the second value, respectively; and generating a variant call.

10 Claims, 2 Drawing Sheets

COMPUTATION PIPELINE OF LOCATION-DEPENDENT VARIANT CALLS

CROSS-REFERENCE TO RELATED APPLICATIONS

This application claims priority to U.S. provisional patent application Nos. 62/139,148, filed Mar. 27, 2015 and 62/143,013, filed Apr. 3, 2015, the disclosure of which is incorporated herein by reference.

FIELD OF THE INVENTION

The present invention generally relates to genomic sequencing data analysis.

BACKGROUND OF THE INVENTION

Next-generation sequencing (NGS) technology has provided a powerful tool to produce a gigantic amount of biological data that will shed light on path towards personalized medicine. While the cost of high throughput genome sequencing is decreasing in terms of merely acquiring sequence data, the analysis and interpretation of these large-scale sequencing data remains to pose a major challenge. To call variants from NGS data, many aligners and variant callers have been developed and composed into diverse pipelines. A typical pipeline contains an aligner and a variant caller: the former maps the sequencing reads to a reference genome, and the latter identifies variant sites and assigns a genotype to the subjects. In going through the pipeline, users often need to set many parameters in order to properly analyze the sequencing data. Importantly, some parameters need to be optimized for accurately calling the variant, e.g., on the basis of the type of cells or the ethnic groups from which the sample is prepared. In particular, the optimal value for a parameter may depend on the location in the genome. For example, the parameters associated with the likelihood of a variant occurrence may depend on the location in the genome. However, due to the enormous computation required for each run of the pipeline, going through the entire variant call pipeline to test the optimal value of the parameter for each location in the genome is practically infeasible. Therefore, there is continuing need to develop new methods and systems to optimize parameter settings on the basis of the location in the genome for analyzing NGS data.

SUMMARY OF THE INVENTION

In one aspect, the present disclosure provides a computer-implemented method for analyzing variants from a plurality of nucleic acid sequence reads using a computation pipeline, said computation pipeline comprises a module depending on a location-dependent parameter. The method comprises executing on a processor the steps of: receiving a plurality of nucleic acid sequence reads comprising at least a first nucleic acid sequence read and a second nucleic acid sequence read; mapping the first nucleic acid sequence read to a first location in a genome; mapping the second nucleic acid sequence read to a second location in the genome, wherein the first location is different from the second location; setting a first value for the location-dependent parameter on the basis of the first location in the genome; setting a second value for the location-dependent parameter on the basis of the second location in the genome, wherein the first value is different from the second value; passing the first nucleic acid sequence read through the module using the first value; passing the second nucleic acid sequence read through the module using the second value; and generating a variant call.

In certain embodiments, the module is a variant call module. In certain embodiments, the location-dependent parameter is a prior probability or a threshold for variant calling. In certain embodiments, the prior probability is a genome-wide SNP probability or an insertion and deletion (Indel) probability.

In certain embodiments, the module is a local alignment module. In certain embodiments, the location-dependent parameter is penalties of base mismatch, gap opening, gap extension or a threshold for alignment candidates.

In certain embodiments, the first and/or second location is in an exon or an intron. In certain embodiments, the first and/or the second location is in the peripheral or central of a cell nuclear.

In certain embodiments, the genome is obtained from an ethnic group or a regional group. In certain embodiments, the genome is obtained from a healthy subject or a subject of a disease. In certain embodiments, the disease is a cancer.

In another aspect, the present disclosure provides a non-transitory computer-readable medium with instructions for analyzing variants from a plurality of nucleic acid sequence reads using a computation pipeline stored thereon, which comprises at least one module depending on a location-dependent parameter. The instructions when executed by a processor, performs the steps comprising: receiving the plurality of nucleic acid sequence reads comprising at least a first nucleic acid sequence read and a second nucleic acid sequence read; mapping the first nucleic acid sequence read to a first location in a genome; mapping the second nucleic acid sequence read to a second location in the genome, wherein the first location is different from the second location; setting a first value for the location-dependent parameter on the basis of the first location in the genome; setting a second value for the location-dependent parameter on the basis of the second location in the genome, wherein the first value is different from the second value; passing the first nucleic acid sequence read through the module using the first value; passing the second nucleic acid sequence read through the module using the second value; and generating a variant call.

In another aspect, the present disclosure provides a computer-implemented method of analyzing variants from a plurality of nucleic acid sequence reads using a computation pipeline, which comprises a mapping module and a variant call module, wherein the variant call module depends on a parameter of prior probability. The method comprises executing on a processor the steps of: receiving the plurality of nucleic acid sequence reads comprising a first nucleic acid sequence read and a second nucleic acid sequence read; mapping the first nucleic acid sequence read to a first location in a genome; mapping the second nucleic acid sequence read to a second location in the genome, wherein the first location is different from the second location; setting a first value for the parameter of prior probability on the basis of the first location in the genome; setting a second value for the parameter of prior probability on the basis of the second location in the genome, wherein the first value is different from the second value; passing the first nucleic acid sequence read through the variant call module using the first value; passing the second nucleic acid sequence read through the variant call module using the second value; and generating a variant call.

In another aspect, the present disclosure provides a non-transitory computer-readable medium with instructions for analyzing variants from a plurality of nucleic acid sequence reads using a computation pipeline stored thereon, which comprises a mapping module and a variant call module, wherein the variant call module depends on a parameter of prior probability. The instructions when executed by a processor, performs the steps comprising: receiving the plurality of nucleic acid sequence reads comprising a first nucleic acid sequence read and a second nucleic acid sequence read; mapping the first nucleic acid sequence read to a first location in a genome; mapping the second nucleic acid sequence read to a second location in the genome, wherein the first location is different from the second location; setting a first values for the parameter of prior probability on the basis of the first location in the genome; setting a second value for the parameter of prior probability on the basis of the second location in the genome, wherein the first value is different from the second value; passing the first nucleic acid sequence read through the variant call module using the first value; passing the second nucleic acid sequence read through the variant call module using the second value; and generating a variant call.

These and other features, aspects, and advantages of the present invention will become better understood with regard to the following description, appended claims and accompanying drawings.

DETAILED DESCRIPTION OF THE INVENTION

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

It is understood that as used herein and in the appended claims, the singular forms "a," "an," and "the" include the plural reference unless the context clearly dictates otherwise. Thus, for example, a reference to a "module" is a reference to one or more modules, and includes equivalents thereof known to those skilled in the art and so forth.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without these specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Definitions

The following definitions are used in the disclosure:

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. In this disclosure, when a range is given as "(a first number) to (a second number)" or "(a first number)–(a second number)," this means a range whose lower limit is the first number and whose upper limit is the second number. For example, 25 to 100 mm means a range whose lower limit is 25 mm, and whose upper limit is 100 mm.

As used herein, the term "nucleic acid sequence read" refers to a nucleic acid sequence determined by a sequencing method. The nucleic acid sequence can be DNA or RNA sequence. In certain embodiments, the nucleic acid reads are genomic DNA sequencing data. In certain embodiments, the nucleic acid reads are exome sequencing data. Classical DNA sequencing method includes chain termination method (Sanger sequencing). In certain embodiments, "nucleic acid read" refers to a nucleic acid sequence determined by next-generation sequencing (high-throughput sequencing) methods, which parallelize the sequencing process, producing thousands or millions of sequence concurrently. Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each nucleic acid read may vary from about about 30 bp to more than 10,000 bp. For example, Illumina sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate nucleic acid read of 10,000 bp to 15,000 bp. Therefore, in certain embodiments, the nucleic acid sequence reads have a length of 30-100 bp, 50-200 bp, or 50-400 bp.

The term "variant" when used in the context of nucleic acid sequence refers to a nucleic acid sequence read that is different from a reference. Typical nucleic acid sequence variant includes without limitation single nucleotide polymorphism (SNP), short deletion and insertion polymorphisms (Indel), copy number variation (CNV), microsatellite markers or short tandem repeats and structural variation.

As used herein, the term "computer-implemented method" means that the method is carried out in a computer, e.g., a computer program executed by a CPU. A computer, as used herein, refers to a device (for general or specific purposes) that can be programmed to perform a set of arithmetic or logical operations automatically. Computers, as used herein, include without limitation personal computers, workstations, servers, mainframes and supercomputers. The computer can be a stand-alone system, networked system or a virtual machine residing in a computing cloud. The methods described herein can be implemented with multithreading or other parallel computing methods.

As used herein, a "computation pipeline" or a "pipeline" refers to a set of data processing elements connected in series, wherein the output of one element is the input of the next element. In certain embodiments, the output of one operation is automatically fed to the next, following operation. As used herein, the elements of a computational pipeline may be called "modules." In certain embodiments, a pipeline is linear and one-directional. In certain embodiments, a primarily one-directional pipeline may have some communication in the other direction. In certain embodiments, a pipeline may be fully bi-directional.

As used herein, a "module" refers to a data processing element within a computation pipeline. A set of modules connects in series to form a computation pipeline. Usually, a module receives an input data, performs certain function based on the input data, and generates an output data, which is then used as an input data for the next following module. In certain embodiments, a module can be further divided into several sub-modules, e.g., connected in series.

The term "parameter," as used herein, refers to a reference, feature or value that users need to set in a computation pipeline or module. When passing a data set through the computation pipeline or module, the reference, feature, or value is passed to a function, procedure, subroutine, command, or program. Related term "location-dependent parameter," when used in the context of a nucleic acid sequence read passing through a module, means a parameter whose value varies on the basis of the location of the nucleic acid sequence read on a reference (e.g., a reference genome).

The term "value" used herein refers to a number or feature set to a parameter. Accordingly, when a computation pipeline is used to analyze nucleic acid sequence data, the number or feature is passed to a function, procedure, command or program of the computation pipeline described in the present disclosure. The exact number or feature that can be set to a parameter can be understood in the context of the module and the parameter discussed infra. For example, the value for a parameter of prior probability that is used in the variant call module can be 0.0005, 0.0008, 0.001 or 0.002. For another example, the value for a parameter of penalty of mismatch that is used in the alignment module can be +1 to +5.

The term "passing" when used in the context of "passing a data set (e.g., nucleic acid sequence reads) through a pipeline or a module" means analyzing the data set using the pipeline or module. Typically, in passing the pipeline or module, the data set is fed to the pipeline or module as in input. The pipeline or module then use the data set to run the function, procedure, command or program contained within and generate an output (e.g., a second data set). In certain embodiments, the output can be used as an input to be fed to a second pipeline or module. In certain embodiments, passing data set through a module also includes using the data set as indirect input for the module. For example, in a computation pipeline comprising at least two modules connected in series, the data set is passed as input to the first module, which generate an output that is passed as input of the second module. In such situation, the data set is regarded as being passed through the second module even though it is not used as direct input of the second module.

The term "non-transitory computer-readable medium" refers to any computer-readable media with the sole exception being a transitory, propagating signal. Non-transitory computer-readable medium includes, without limitation, a volatile memory, a nonvolatile memory, a soft disk, a hard disk, a memory stick, a register memory, a processor cache and a RAM.

The term "mapping" or "mapping to a reference," as used herein, means aligning nucleic acid sequence reads to a reference, e.g., a reference genome, whose sequence is already known. Various programs and algorithms have been developed to map nucleic acid sequence reads to a reference (see, Flicek P, Birney E. (2009) Sense from sequence reads: methods for alignment and assembly, Nat Methods 6(11 Suppl): S6-S12; Neilsen R, Paul J S et al. (2011) Genotype and SNP calling from next-generation sequencing data. Nat Rev Genet 12: 443-52; Ruffalo M et al. (2011) Comparative analysis of algorithms for next-generation sequencing read alignment. Bioinformatics 27: 2790-96; Patnaik S et al. (2012) Customisation of the exome data analysis pipeline using a combinatorial approach. PLoS ONE 7: e30080). Among the various programs and algorithms, Burrows-Wheeler Aligner (BWA), which is based on Burrows-Wheeler transformation, (Li H, Durbin R (2009) Fast and accurate short rad alignment with Burrows-Wheeler transform. Bioinformatics 25: 1754-60) demonstrates a good balance between running time, memory usage and accuracy, and commonly used in different computation pipelines.

Computation Pipeline for Analyzing Nucleic Acid Sequence Reads

Rapid advances in next-generation sequencing technologies have transformed biological and biomedical research over the past several years. Depending on the sequencing method and system used, the number of nucleic acid reads generated is often more than several million. For example, MiniSeq System from Illumina generates up to 25 million reads per run, and the HiSeq series from Illumina generates up to 5 billion reads per run. With the gigantic amount of sequencing data generated, there is an imminent need for powerful computational tools to analyze and interpret these large-scale sequencing data.

Many computation pipelines composed of various aligners and variant callers have been developed, including, without limitation, SAMtools (Li H et al. (2009) The sequence alignment/Map format and SAMtools. Bioinformatics 25: 2078-79), glftools (Abecasis lab (2010) Abecasis lab GLF tools), GATK (DePristo M A et al. (2011) A framework for variation discovery and genotyping using next-generation DNA sequencing data. Nat Genet 43: 491-98; McKenna A et al. (2010) The genome analysis Toolkit: a MapReduce framework for analyzing next-generation DNA sequencing data. Genome Res 20: 1297-1303) and Atlas (Challis D et al. (2012) An integrative variant analysis suite for whole exome next-generation sequencing data. BMC Bioinformatics 13: 8).

Figure 1:
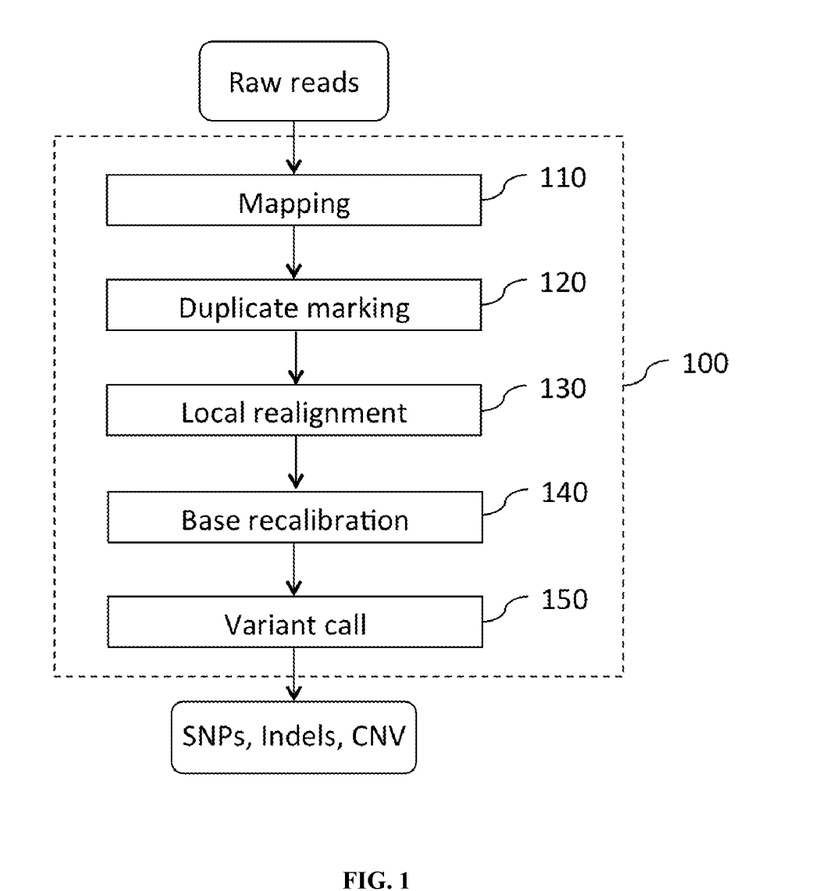
FIG. 1 shows an exemplary computation pipeline.

An exemplary computation pipeline for analyzing nucleic acid sequence reads is illustrated in FIG. 1. As shown in FIG. 1, a computation pipeline 100 for analyzing nucleic acid sequence reads comprises an array of modules connected in series.

Initially, raw read data are fed to the mapping module 110 to align the short sequencing reads to a reference. The mapping module 110 aligns the nucleic acid sequence reads to a reference, e.g., a reference genome, whose sequence is already known. Various programs and algorithms have been developed to map nucleic acid sequence reads to a reference (see, Flicek P, Birney E. (2009) Sense from sequence reads: methods for alignment and assembly, Nat Methods 6(11 Suppl): S6-S12; Neilsen R, Paul J S et al. (2011) Genotype and SNP calling from next-generation sequencing data. Nat Rev Genet 12: 443-52; Ruffalo M et al. (2011) Comparative analysis of algorithms for next-generation sequencing read alignment. Bioinformatics 27: 2790-96; Patnaik S et al. (2012) Customisation of the exome data analysis pipeline using a combinatorial approach. PLoS ONE 7: e30080). Among the various programs and algorithms, Burrows-Wheeler Aligner (BWA), which is based on Burrows-Wheeler transformation, (Li H, Durbin R (2009) Fast and accurate short rad alignment with Burrows-Wheeler transform. Bioinformatics 25: 1754-60) demonstrates a good balance between running time, memory usage and accuracy, and are commonly used in different computation pipelines.

The output (e.g., a SAM (Sequence Alignment/Map) file or a BAM (binary version of SAM) file) of the mapping module is then fed to the duplicate marking module 120 to remove PCR duplicate. During the preparation of DNA samples for sequencing, PCR is often used to amplify the fragments, thus generating duplicates. Ideally prepared samples often generate several percent (e.g., about 4%) reads that are identical copies of each other, i.e., duplicates. Sometime, 30% to 70% of the reads are duplicates. Algorithms for marking/removing duplicates have been described by Wysoker A et al (PicardTools) and Li H et al (Li H et al. (2009) The sequence alignment/Map format and SAMtools. Bioinformatics 25: 2078-79).

The reads with duplicates marked/removed is fed to a local realignment module 130 to improve on the alignments of the reads. Typically, realignment occurs in areas around insertions and deletions (Indel) in the reads relative to the reference and is to map the read with one end on one side of the Indel and the rest on the other side. When the reads are originally mapped to the reference, no information is available about the existence of an Indel. Thus, reads that are mapped to such regions, but that only have a short part of the read representing the region on one side of the Indel, will typically not be mapped properly across the Indel, but instead be mapped with this end unaligned, or into the Indel region with many mismatches. The local alignment module 130 uses information from the other reads mapping to a region containing an Indel, including reads that are located more centered across the Indel and thus have been mapped with ends on either side of the Indel. As a result, an alternative mapping, as good as or better than the original, can be generated.

Algorithms for local realignment have been described by Homer et al. (Homer N (2010) Improved variant discovery through local re-alignment of short-read next generation sequencing data using srma. Genome Biol 11(10): R99). In the first step, alignment information of all input reads are collected in an efficient graph-based data structure, which is essentially similar to a de-Bruijn graph. This realignment graph represents how reads are aligned to the reference sequence and how reads overlap each other. In the second step, metadata are derived from the graph structure that indicate at which alignment positions realignment could potentially improve the read mapping, and also provides hypotheses as to how reads should be realigned to yield the most concise multiple alignment. In the third step the realignment graph and its metadata are used to actually perform the local realignment of each individual read.

DePristo et al. described an alternative algorithm for local realignment (DePristo M A et al. (2011) A framework for variation discovery and genotyping using next-generation DNA sequencing data. Nat Genet 43: 491-98). The algorithm begins by first identifying regions for realignment where (i) at last one read contains an Indel, (ii) there exists a cluster of mismatching bases or (iii) an already known Indel segregates at the site (e.g., from dbSNP (single nucleotide polymorphism database), which is a public archive for genetic variation within and across different species developed and hosted by the National Center for Biotechnology Information (NCBI), which contains a range of molecular variation including (1) SNPs; (2) short deletion and insertion polymorphisms, (3) microsatellite markers or short tandem repeats (STRs), (4) multinucleotide polymorphisms (MNPs), (5) heterozygous sequences, and (6) named variants). At each region, haplotypes are constructed from the reference sequence by incorporating any known Indels at the site, Indels in reads spanning the site or from Smith-Waterman alignment of all reads that do not perfectly match the reference sequence (Durbin et al. (1998) Biological Sequence Analysis: Probabilistic Models of Proteins and Nucleic Acids. (Cambridge University Press, Cambridge, UK)). For each haplotype Hi, reads are aligned without gaps to Hi and scored according to:

$$L(R_j \mid H_i) = \prod_k L(R_{j,k} \mid H_{i,k})$$

$$L(R_{j,k} \mid H_{i,k}) = \begin{cases} 1 - \varepsilon_{j,k} \approx 1 & R_{j,k} = H_{i,k} \\ \varepsilon_{j,k} & R_{j,k} \neq H_{i,k} \end{cases}$$

$$L(H_i) = \prod_j L(R_j \mid H_i)$$

wherein Rj is the jth read, k is the offset in the gapless alignment of Rj and Hi and $\varepsilon_{jk}$ is the error rate corresponding to the declared quality score for the kth base of read Rj, The haplotype Hi that maximizes L(Hi) is selected as the best alternative haplotype. Next, all reads are realigned against just the best haplotype Hi and the reference ($H_0$), and each read Rj is assigned to Hi or $H_0$ depending on whichever maximizes L(Rj|H). The reads are realigned if the log odds ratio of the two-haplotype model is better than the single reference haplotype by at least five log units:

$$\frac{L(H_0, H_i)}{L(H_0)} = \frac{\prod_j \max[L(R_j | H_i), L(R_j | H_0)]}{\prod_j L(R_j | H_0)}$$

This discretization reflects a tradeoff between accuracy and efficient calculation of the full statistical quantities. In certain example, the algorithm operates on all reads across all individuals simultaneously, which ensures consistency in the inferred haplotypes among all individuals, a critical property for reliable Indel calling and contrastive analyses such as somatic SNP and Indel calling. Typically, the realigned reads are written to a SAM/BAM file for further analysis.

The output of the local realignment module is then fed to the base recalibration module 140, which provides empirically accurate base quality scores for each base in every read. In certain examples, the base recalibration module 140 also corrects for error covariates like machine cycle and dinucleotide context, as well as supporting platform-specific error covariates like color-space mismatches for SOLiD and flow-cycles for 454. Exemplary algorithm for base recalibration module 140 has been described by DePristo M A et al. (DePristo M A et al. (2011) A framework for variation discovery and genotyping using next-generation DNA sequencing data. Nat Genet 43: 491-98). Typically, for each lane, the algorithm first tabulates empirical mismatches to the reference at all loci not known to vary in the population (dbSNP build 129), categorizing the bases by their reported quality score (R), their machine cycle in the read (C) and their dinucleotide context (D). The empirical quality score for each category can be estimated as the following:

$$\text{mismatch}(R, C, D) = \sum_{r \in R}\sum_{c \in C}\sum_{d \in D}\sum_{b r, c, d} br, c, d \neq bref$$

$$\text{bases}(R, C, D) = \sum_{r \in R}\sum_{c \in C}\sum_{d \in D} |\{b, r, c, d\}|$$

$$Q_{empirical}(R, C, D) = (\text{mismatch}(R, C, D) + 1) / (\text{bases}(R, C, D) + 1)$$

The covariates are then broken into linearly separable error estimates and the recalibrated quality score $Q_{recal}$ is calculated as:

$$\text{recal}(r, c, d) = Qr + \Delta Q(r) + \Delta\Delta Q(r, c) + \Delta\Delta Q(r, d)$$

$$\Delta Q = Q_{empirical}(R, C, D) - \left(\sum_p \varepsilon_r \times N_r\right) / \text{bases}(R, C, D)$$

$$\Delta Q(r) = Q_{empirical}(r, C, D) - Q_r - \Delta Q$$

$$\Delta Q(r, c) = Q_{empirical}(r, c, D) - (\Delta Q_r + \Delta Q(r))$$

$$\Delta Q(r, d) = Q_{empirical}(r, C, d) - (\Delta Q_r + \Delta Q(r))$$

where each $\Delta Q$ and $\Delta\Delta Q$ are the residual differences between empirical mismatch rates and that implied by the reported quality score for all observations conditioning only on $Q_r$ or on both the covariate and $Q_r$; wherein $Q_r$ is the base's reported quality score and $\varepsilon_r$ is its expected error rate; $b_{r,c,d}$ is a base with specific covariate values, and r, c, d and R, C, D are the sets of all values of reported quality scores, machine cycles and dinucleotide contexts, respectively.

The output from the base recalibration module 140 is then fed to variant call module 150 to discover all sites with statistical evidence for an alternate allele present among the reads including SNPs, short indels and copy number variations. Typically, a variant call module uses an algorithm or statistical model that is usually specified by mathematical equations that relate one or more random variables and possibly other non-random variables. For example, based on the read depths and variant counts, a probability value indicating the confidence level that a specific variant at a specific location is a true positive is calculated using a statistical model based method and a localized method using a reference sample.

Various algorithms have been developed for variant calling. For example, Mapping and Assembly with Quality (MAQ) (Li H et al. (2008) Mapping short DNA sequencing reads and calling variants using mapping quality scores. Genome Res 18: 1851-58) and SOAPsnp (Li R et al. (2009) SNP detection for massively parallel whole-genome resequencing. Genome Res 19: 1124-32) use fixed prior probability value for heterozygote and nucleotide-read error. SeqEM (Martin E R et al. (2010) SeqEM: an adaptive genotype-calling approach for next generation sequencing studies. Bioinformatics 26: 2803-10) introduces multiple-sample genotype calling via an adaptive approach employing the expectation-maximization (EM) algorithm to estimate the model parameters. SAMtools uses a revised MAQ model to estimate sequencing error. The glftools family (glfSingle, glfMultiples, and polymutt) call SNPs from pre-generated genotype likelihood files (GLF). GATK adopts the MapReduce philosophy to parallel programming for simple Bayesian modeling (Dean J, Ghemawat S (2008) MapReduce: simplified data processing on large clusters. Commu ACM 51: 107-13). Atlas2 employs logistic regression models trained on validated whole-exome capture sequencing data rather than regular likelihood calculation s and has been shown to have high sensitivity (Ji H P (2012) Improving bioinformatics pipelines for exmome variant calling. Genome Med 4: 7).

In certain embodiments, the sequence of the modules in the computation pipeline described above can be shuffled. For example, the duplicate marking module can be placed downstream of the local realignment module.

In certain embodiments, a computation pipeline may have fewer modules as described above. For example, Liu X et al described a pipeline that skips local realignment module, duplicate marking module and base recalibration module (Liu X et al. (2013) Variant callers for next-generation sequencing data: a comparison study. PLoS ONE 8(9): e75619).

Computation Pipeline of Location-Dependent Setting

In passing the reads through a computation pipeline, the users need to set values to many parameters. For example, in a variant call module, the user needs to specify certain prior probabilities. "Prior probability" refers to the probability distribution representing prior knowledge about the distribution of variants, which is incorporated to facilitate variant calling. In a variant call module adopting GATK algorithm, for example, the user needs to specify the genome-wide SNP probability and the Indel probability. The "genome-wide SNP probability" means the probability of a variation in a single nucleotide that may occur at some specific position in the genome, where each variation is present to some appreciable degree within a population. The "Indel probability" refers to the probability of the occurrence of an insertion or the deletion of bases in the DNA of an organism. Similarly, in a variant call module using SAMTools algorithm, the user needs to specify Phread-scaled gap extension sequencing error probability and Phred-scaled gap open sequencing error probability.

There are many other parameters that users need to set in the pipeline. For example, in a local alignment module, the user needs to specify the penalties for mismatch (a scoring system used for aligning a small portion of fragmented genetic sequence, e.g., in order to make more accurate decisions in aligning reads, mutations are annotated as gaps in the sequence, and gaps are penalized via various penalty scoring methods, which allows for the optimization of sequence alignment in order to obtain the best alignment possible based on the information available), gap opening (the cost required to open a gap of any length) and gap extension (the cost required to extend the length of an existing gap). In base quality recalibration, the user needs to specify the recalibration table (a table built up to track the number of matches/mismatches for each set of covariates and to assign a well-calibrated probability to each variant call in a call set) or the parameters to compute the recalibration table, and quantization level in the base quality output. The user may also need to specify variant call mode (the value that appears most often in a set of data representing an estimate of variant frequency and some measure of confidence) and thresholds for variant calling (the minimum confidence threshold at which the program should emit variant sites as called; if a site's associated genotype has a confidence score lower than the calling threshold, the program will emit the site as filtered; this threshold separates high confidence calls from low confidence calls), pair-HMM (pair-hidden Markov Model, a variant of the basic HMM that is especially useful for finding sequence alignments and evaluating the significance of the aligned symbols) and the transition probability used therein, etc.

For some of the parameters, their optimal value may depend on the location in the genome. These parameters include, but are not limited to: the prior probabilities; the penalties for mismatch, gap opening, gap extension during local alignment and pair-HMM; and threshold for variant calling; etc. These parameters are associated with the likelihood of a variant occurrence, and are dependent on the location within the genome.

For example, it is known that variant occurrence frequency in exon regions is lower than that in intron regions (Zhao et al. (2003) Investigating single nucleotide polymorphism (SNP) density in the human genome and its implications for molecular evolution. Gene 312:207-13). The variant occurrence frequency may also vary in different chromosomes and chromosome regions. Therefore, it is desirable to take the location in the genome into consideration when setting values to the location-dependent parameter. For example, a more accurate description of prior probabilities, for either SNP or Indel or both, would be a map based on the reference genome, i.e., a map of prior probabilities that describes the variant occurrence frequency in all locations across the entire genome. In certain embodiment, such a map that describes a parameter's optimal value across the genome is called a Parameter Map (PM).

In certain embodiments, the PM is also customized for an ethnic group, e.g., Caucasians, Asians, etc. In certain embodiments, the PM is customized for a population of a country or in a region, e.g., Japanese, British, etc.

In certain embodiments, the PM is customized for a population of certain diseases or disorders. For example, the PM can be customized for certain cancer patients, e.g., breast cancer, liver cancer patients.

In certain embodiments, the PM is customized for certain cell types, e.g., skin cells, blood cells, etc.

In certain embodiments, a PM for prior probabilities can be generated by analyzing a large number of genomes to collect the variant occurrence frequency, e.g., SNP or indel, for each and all locations across the genome. In certain embodiments, a PM for an ethnic group, e.g., Caucasians, Asians, etc., is produced by analyzing genomes of such ethnic group. Similarly, a PM for particular cell types or disease/disorder groups can also be generated by analyzing the genomes from such cell types of disease/disorder groups.

Therefore, in one aspect, the present disclosure provides methods and systems of analyzing variants from a plurality of nucleic acid sequence reads using a computation pipeline that comprises a module depending on a location-dependent parameter. The method comprises executing on a processor the steps of: receiving the plurality of nucleic acid sequence reads comprising at least a first nucleic acid sequence read and a second nucleic acid sequence read; mapping the first nucleic acid sequence read to a first location in a genome; mapping the second nucleic acid sequence read to a second location in the genome, wherein the first location is different from the second location; setting a first value for the location-dependent parameter on the basis of the first location in the genome; setting a second value for the location-dependent parameter on the basis of the second location in the genome, wherein the first value is different from the second value; passing the first nucleic acid sequence read through the module using the first value; passing the second nucleic acid sequence read through the module using the second value; and generating a variant call.

Figure 2:
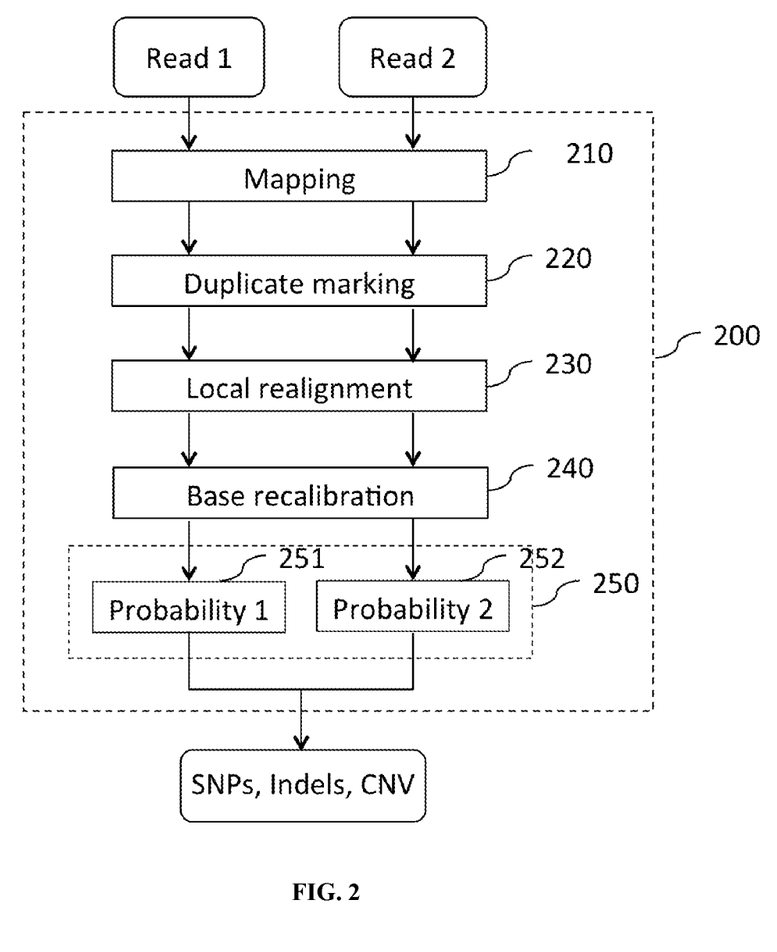
FIG. 2 shows an exemplary computation pipeline comprising a module depending on a location-dependent parameter.

An exemplary computation pipeline comprising a module depending on a location-dependent parameter is illustrated in FIG. 2. As shown in FIG. 2, a computation pipeline 200 for analyzing nucleic acid sequence reads comprises an array of modules connected in series.

Raw read data comprising Read 1 and Read 2 are fed to the mapping module 210 to align the short sequencing reads to a reference genome. Read 1 is mapped to Location 1 (e.g., exon) of the reference genome, and Read 2 is mapped to Location 2 (e.g., intron) of the reference genome. The output of the mapping module 210 is fed to the duplicate marking module 220, whose output is fed to the local realignment module 230. The output of the local realignment module 230 is fed to base recalibration module 240. The output of the base recalibration module 240 is fed to the variant call module 250. When the input data is passed through the variant call module 250, values are set to the parameter, e.g., prior probabilities, on the basis of the location of the reads. As illustrated, when Read 1 is passed through the variant call module 250, a first value is set to the prior probabilities (e.g., SNP probability of 0.0005 for exon region (see Zhao et al. (2003) Investigating single nucleotide polymorphism (SNP) density in the human genome and its implications for molecular evolution. Gene 312:207-13)). When Read 2 is passed through the variant call module 250, a second value is set to the prior probabilities (e.g., SNP probability of 0.0008 for intron region). A variant call is then produced.

In a typical variant call pipeline used currently, a single set of prior probabilities (e.g., overall average variant frequency) is used across the entire genome. As a result, extra unnecessary variants are called in regions that have low prior-probability (e.g., in exons), and variant calls in high-prior probability regions (e.g., in intron) are missed. Adjusting the prior-probability parameter, as long as there is only a single set of value across the whole genome, will only sacrifice certain regions to benefit others. No optimal calling can be achieved simultaneously across the entire genome.

In the example described above, by using different prior probabilities according to the read's location in the genome, each variant is called using its optimal prior probability that depends on its location in the genome, e.g., exon or intron region. Such a location-dependent variant call significantly improves variant calling accuracy.

Further, if the type of the new genome is known, e.g., ethnicity, and/or whether it is a cancer sample and its cell type, a different PM may be selected for the pipeline. This selection process may also be automated: the pipeline can compute and output results using a general set of parameters in the first pass. From the results of the first pass, certain additional information, e.g., ethnicity, may be identified. Then the pipeline is run again, but with a PM based on the information obtained from the first pass, to improve the overall variant calling accuracy. This can be even done in multiple passes, if necessary.

Using the above-described location-dependent variant call method, a multi-pass iterative procedure can be used to improve the PMs themselves. For a certain type of genome (ethnicity, cancer cell type, etc), a set of genome data of the type is initially passed through the pipeline using a general parameter set as first pass. The initial prior-probability PM is generated by averaging the variant occurrence frequency over the dataset at each location of the genome. The entire dataset is then passed through the pipeline for a second time using the PM that is generated from the results of the first pass, so to improve the accuracy of the variant call. Then a second prior-probability PM can be generated using the results of the second pass. The second prior-probability PM so generated can be applied to a third pass. This iterative process can continue until the PM converges, that is, the difference between the PMs of the $n_{th}$ and the $(n-1)_{th}$ passes is below a certain threshold. Such converged PMs are optimal on the given genome dataset.

In addition to prior probabilities, the optimal values of some other parameters may also depend on the location in genome, e.g., the penalties for mismatch, gap opening, and gap extension used during local realignment. These penalty numbers are related to the probabilities of occurrence of SNP and Indel, hence may be correspondingly adjusted to create their PMs. Other parameters whose optimal values also depend on the genome location include threshold for variant calling. Similar to the prior-probability parameter, by using PMs of these parameters, variant call based on the location-dependent optimal value for these parameters can be realized.

In certain embodiments, PMs are used in pipeline steps other than the variant call, e.g., in the alignment step. During alignment, some parameters are also selected by users, for example, the penalties for mismatch, gap opening, and gap extension for the inexact alignment, the threshold for alignment candidates, etc. The optimal values for these parameters may also be location dependent, so the application of PMs for these parameters also improves the alignment performance.

In certain embodiment, location-dependent PM is also applied to RNAseq pipelines, i.e., using genome location-dependent PM to improve RNAseq pipeline accuracy.

Computation Pipeline of
Single-Pass-Multiple-Parameter-Map

Another aspect of the disclosure provides methods and systems in which multiple variant calls using a plurality of parameter maps are implemented in a single-pass pipeline.

In certain embodiments, the user is unsure about the exact sample characteristics, e.g., the ethnicity, or whether it is cancer sample or not, etc. In such case, the user may choose to run variant calls using multiple PMs. In certain embodiments, even though the type of the current genome sample is known, the user may still want to explore different PMs in order to study how the variants may change under different assumptions for the sample. One way to explore the multiple PMs is to pass the sequencing data through the entire pipeline for multiple times for each PM, which costs enormous computation. In order to save computation cost and time, the user may pass the sequencing data through the pipeline for a single time while running the variant call module for multiple times using the multiple PMs.

In such a single pass multi-setting pipeline, many computations that are common to the different variant calls can be done only once and re-used, vastly reducing the overall computation time and cost in exploring a large number of PM selections. For example, if the users only want to explore a few different PMs for prior-probability, they may select a list of the maps. In an exemplary embodiment, the first few sub-steps of the pipeline that do not depend on the prior-probability parameters are performed only once, while the statistical model is run multiple times—once under each PM. Furthermore, some of the computations in the statistical model itself also do not depend on the prior probabilities, so can also be run only once, for example, read filtering which only depends on read base qualities and alignments, and certain conditional probabilities of bases given base quality and genotype. In summary, all common computations that do not depend on the varied PMs can be run only once, and then be re-used among the multiple variant calls. By removing all the redundant computations, we can output the called variant's properties under all the different PMs in a single pass pipeline, while controlling the total computation to only a small fraction of the computation otherwise required by running the full pipeline for each PM selection. After this single-pass multiple-map run, the called variant's properties (e.g., its probability) can be visually displayed as a function of the PM selection, enabling users to have a better visual understanding of the variants. This single-pass multiple-map pipeline method can be applied to many scenarios of PM exploration, to reduce computation by reusing common intermediate results among the different PMs. Also, it not only applies to the DNA assembly pipeline, but can also be used in RNAseq pipelines, to achieve single-pass multiple-map exploration with affordable computation requirements.

This single-pass multiple-map pipeline method can also be used in the alignment-to-reference computation. When users explore the alignment PMs, the reads that have perfect match with the reference do not need to be re-run through the alignment under different alignment PM, but can be done once and used for all PMs. Only unmapped reads and the reads that have mismatches with the reference need to go through multiple alignments under the different PMs.

Computation Pipeline of Incremental Exploration

In certain embodiments, the location-dependent pipeline described herein can be used in an incremental exploration mode. Instead of computing and outputting results of many PMs in a single pass, the pipeline can compute and output results under a single PM in a first pass, while also saving many intermediate results of the first pass. If the user decides to explore additional PMs, the pipeline can automatically identify those intermediate results that do not need to be re-computed, and use them directly in the new pass. As such, the additional pass with the new PM only computes those portions of the pipeline that are affected by the difference between the new and previous PMs, hence saving computations in PM exploration even if it is not a single pass. In certain embodiments, this mode is preferable because the user may make decisions on further PM explorations after reviewing the results from earlier PMs, possibly eliminating the exploration of some unnecessary PMs.

In certain embodiments, the two use modes, namely the "single-pass-multiple-PM" and the "incremental exploration" mode can be further combined. In such combination mode, the sequencing data is passed through the pipeline using multiple PMs in the first single pass, and the intermediate results are saved. After reviewing the results from the first pass, the user may decide to explore additional PM or PMs in a second pass of the pipeline. In the second pass, the pipeline can re-use the intermediate results from the first pass, hence saving computation in the new pass.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A computer-implemented method for analyzing variants from a plurality of nucleic acid sequence reads using a computation pipeline, said computation pipeline comprising a parameter of SNP or insertion and deletion (Indel) probability, said method comprising executing on a processor the steps of:

receiving at least a thousand nucleic acid sequence reads comprising at least a first nucleic acid sequence read and a second nucleic acid sequence read;

mapping the at least a thousand nucleic acid sequence reads to locations in a genome, respectively, wherein
      the first nucleic acid sequence read is mapped to a first location,
      the second nucleic acid sequence read is mapped to a second location, and
      the first location is different from the second location;

setting values for the parameter of SNP or Indel probability on the basis of the locations in the genome, respectively, wherein a first value set at the first location is different from a second value set at the second location;

passing the at least a thousand nucleic acid sequence reads through the computation pipeline, using values set for the parameter of SNP or Indel probability; and generating a variant call.

2. The method of claim 1, wherein the first and/or second location is in an exon or an intron.

3. The method of claim 1, wherein the genome is obtained from an ethnic group or a regional group.

4. The method of claim 1, wherein the genome is obtained from a healthy subject or a subject of a disease.

5. The method of claim 4, wherein the disease is a cancer.

6. A non-transitory computer-readable medium with instructions for analyzing variants from a plurality of nucleic acid sequence reads using a computation pipeline stored thereon, said computation pipeline comprising a parameter of SNP or Indel probability, said instructions when executed by a processor, performing the steps comprising:

receiving at least a thousand nucleic acid sequence reads comprising at least a first nucleic acid sequence read and a second nucleic acid sequence read;

mapping the at least a thousand nucleic acid sequence reads to locations in a genome, respectively, wherein
      the first nucleic acid sequence read is mapped to a first location,
      the second nucleic acid sequence read is mapped to a second location, and
      the first location is different from the second location;

setting values for the parameter of SNP or Indel probability on the basis of the locations in the genome, respectively, wherein a first value set at the first location is different from a second value set at the second location;

passing the at least a thousand nucleic acid sequence reads through the computation pipeline, using the values set for the parameter of SNP or Indel probability; and generating a variant call.

7. The method of claim 6, wherein the first and/or second location is in an exon or an intron.

8. The method of claim 6, wherein the genome is obtained from an ethnic group or a regional group.

9. The method of claim 6, wherein the genome is obtained from a healthy subject or a subject of a disease.

10. The method of claim 9, wherein the disease is a cancer.

* * * * *